United States Patent
Mori et al.

(10) Patent No.: US 8,577,112 B2
(45) Date of Patent: Nov. 5, 2013

(54) MRI METHODS USING DIFFUSION TENSOR IMAGING TECHNIQUES AND MRI SYSTEMS EMBODYING SAME

(75) Inventors: Susumu Mori, Ellicott City, MD (US); Hangyi Jiang, Cockeysville, MD (US); Ming-Chung Chou, Taichung County (TW); Yue Li, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 906 days.

(21) Appl. No.: 12/489,682

(22) Filed: Jun. 23, 2009

(65) Prior Publication Data
US 2009/0290770 A1 Nov. 26, 2009

Related U.S. Application Data

(63) Continuation-in-part of application No. PCT/US2007/026321, filed on Dec. 26, 2007.

(60) Provisional application No. 60/877,311, filed on Dec. 27, 2006.

(51) Int. Cl.
*G06K 9/00* (2006.01)
(52) U.S. Cl.
USPC .......................... 382/131; 600/410; 324/307
(58) Field of Classification Search
USPC ............................. 382/131; 600/410; 324/307
See application file for complete search history.

(56) References Cited

U.S. PATENT DOCUMENTS

| | | | |
|---|---|---|---|
| 5,933,139 A | 8/1999 | Feigner et al. | |
| 6,519,860 B1 | 2/2003 | Bieg et al. | |
| 6,724,190 B2 | 4/2004 | Van Muiswinkel et al. | |
| 6,859,203 B2 | 2/2005 | Van Muiswinkel et al. | |
| 7,358,730 B2 * | 4/2008 | Mistretta et al. | 324/307 |
| 8,406,849 B2 * | 3/2013 | Jeong et al. | 600/410 |
| 2005/0240097 A1 | 10/2005 | Lange | |
| 2008/0054899 A1 * | 3/2008 | Aksoy et al. | 324/307 |

OTHER PUBLICATIONS

Skare "Optimisation Strategies in Diffusion Tensor MR Imaging", 2002, MR Center, Dept. of Clinical Neuroscience, Karolinska Institutet, Stockholm, Sweden, Karolinska University Press.*

Behrens et al., "Characterization and Propagation of Uncertainty in Diffusion-Weighted MR Imaging" 2003, Magnetic Resonance in Medicine vol. 50, 1077-1088.*

(Continued)

*Primary Examiner* — David Zarka
*Assistant Examiner* — Katrina Fujita
(74) *Attorney, Agent, or Firm* — Edwards Wildman Palmer LLP; Peter F. Corless; Richard B. Emmons (57) ABSTRACT

Featured is a method for automatically evaluating acquired MRI data, determining the quality of the acquired images and removing the image data when it is determined that an image is corrupted so the imaged data for the corrupted image is removed from the subsequent tensor fitting. In further embodiments, such determining includes judging the quality of the image data to determine if the image data satisfies a quality threshold criteria and if determined not to be satisfied adjudging the image to be corrupted. Such methods include performing said evaluating, determining and removing in real time and in the case where an image is determined to be corrupted, such methods further includes re-acquiring additional image data corresponding to each of the one or more images removed as being corrupted. Also featured are MRI systems embodying such methods.

18 Claims, 6 Drawing Sheets

(56) References Cited

OTHER PUBLICATIONS

Rohde et la., "Estimating intensity variance due to noise in registered images: Applications to diffusion tensor MRI", 2005, NeuroImage vol. 26, 673-684.*

Benner et al., "Real-Time RF Pulse Adjustment for B0 Drift Correction", Jun. 2006, Magnetic Resonance in Medicine 56:204-209.*

Chang et al., "RESTORE: Robust Estimation of Tensors by Outlier Rejection", 2005, Magnetic Resonance in Medicine 53:1088-1095.*

Liu et al., "Self-Navigated Interleaved Spiral (SNAILS): Application to High-Resolution Diffusion Tensor Imaging", 2004, Magnetic Resonance in Medicine 52:1388-1396.*

* cited by examiner

MRI METHODS USING DIFFUSION TENSOR IMAGING TECHNIQUES AND MRI SYSTEMS EMBODYING SAME

This application is a continuation in part of co-pending PCT Application No. PCT/US2007/026321, filed Dec. 26, 2007, which application claims the benefit of U.S. Provisional Application Ser. No. 60/877,311 filed Dec. 27, 2006, the teachings of all being incorporated herein by reference.

STATEMENT REGARDING FEDERALLY-SPONSORED RESEARCH

The present invention was supported by grants from the National Institute of Health, grant number RR015241. The U.S. Government may have certain rights to the present invention.

FIELD OF INVENTION

The present invention relates to a methods of magnetic resonance imaging and more particularly to magnetic resonance imaging using diffusion tensor imaging techniques. The present invention also relates to computer readable mediums and MRI systems with applications programs embodying such methods.

BACKGROUND OF THE INVENTION

Diffusion tensor imaging (DTI) is a relatively new modality in Magnetic Resonance Imaging (MRI). The DTI Magnetic Resonance Imaging (DTI-MRI) technique is used because of the capability to depict white matter tracts and for its sensitivity to micro-structural and architectural features of brain tissue. As such, because of the ability of DTI-MRI to delineate detailed anatomy of the white matter, it is becoming a widely-used imaging method in research and clinical studies.

According to this method, diffusion constant of water molecules are measured along multiple orientations. If the imaged sample has ordered anatomical structures, such as axonal bundles in the brain, water tends to diffuse along such structures. Consequently, results of diffusion constant measurements of the brain are not the same depending on the orientations of the measurements. This is called anisotropic diffusion. The extent of the anisotropy and the orientation of the largest diffusion constant, assuming that it represent the orientations of the axonal bundles, carry unique anatomical information, which has not been accessible by conventional MRI.

In the conventional DTI-MRI method, diffusion tensor maps are typically computed by fitting the signal intensities from diffusion weighted images as a function of their corresponding b-matrices [Mattiello J, Basser P J, Le Bihan D. The b matrix in diffusion tensor echo-planar imaging. Magn Reson Med 1997; 37:292-300] according to the multivariate least-squares regression model proposed by Basser et al. [Basser P J, Mattiello J, LeBihan D. Estimation of the effective self-diffusion tensor from the NMR spin echo. J Magn Reson B 1994; 103: 247-254]. The least-squares (LS) regression model takes into account the signal variability produced by thermal noise by including the assumed signal variance as a weighting factor in the tensor fitting.

While it is a highly useful MRI technique to investigate normal and abnormal brain anatomy, it has several drawbacks. Signal variability in diffusion weighted imaging (DWI) is influenced not only by thermal noise but also by spatially and temporally varying artifacts. Such artifacts originate from the so called "physiologic noise" such as subject motion and cardiac pulsation, as well as from acquisition-related factors such as system instabilities. The multivariate least-squares regression model assumes that the signal variability in the DWI is affected only by thermal noise and does not account for signal perturbations and potential outliers that originate from artifacts. While the signal variability produced by thermal noise is approximately Gaussian distributed [Henkelman R M. Measurement of signal intensities in the presence of noise in MR images. Med Phys 1985; 12:232-233], signal variability produced by physiologic noise and other artifacts does not have a known parametric distribution and thus currently cannot be modeled.

Figure 1A:
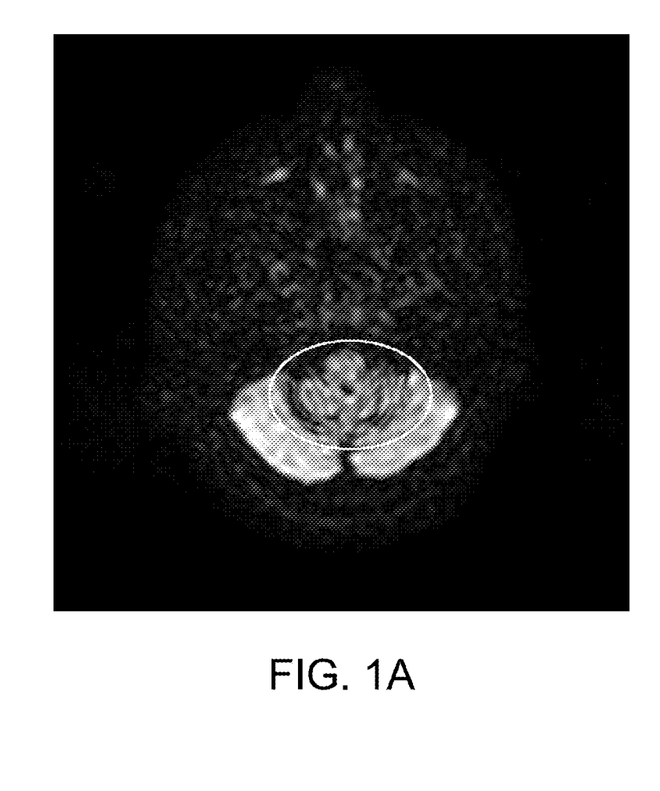
FIGS. 1A,B are illustrations of a corrupted image (FIG. 1A) and an uncorrupted image (FIG. 1B)

For example, one of the most significant issues is the technique's sensitivity to tissue motion. Because water molecules moves 5-10 μm during the measurement and the image contrast is sensitized to such a small motion, the image could be easily corrupted by even a small amount of brain motion, such as cardiac pulsation. To ameliorate this issue, single-shot rapid imaging is usually used for DTI-MRI data acquisition. However, even with such rapid imaging, it is very common that the dataset contains several corrupted images such as that shown in, for example, FIG. 1A.

In the DTI technique only 7 images (one non-diffusion weighted image and six different diffusion weighting orientations) are required to perform the diffusion tensor fitting. However, to enhance signal-to-noise ratio (SNR) one acquires raw images far more than necessary; for the tensor fitting, typically on the order of 12-90 images are acquired by repeating the six different diffusion weighted imaging conditions or by acquiring diffusion weighted images with more than six different weighting orientations.

A couple of techniques or schemes have been described which use or apply a routine fitting outlier detection scheme to DTI-MRI. These techniques have been described as the use of "robust" estimators, which are less sensitive to the presence of outliers. One robust tensor estimation approach, as proposed by Mangin et al. [Mangin J F, Poupon C, Clark C, Le Bihan D, Bloch I. Distortion correction and robust tensor estimation for MR diffusion imaging. Med Image Anal 2002; 6:191-198], is based on the well-known Geman-McClure M-estimator [Geman S, McClure D E. Statistical methods for tomographic image reconstruction. Bull Int Stat Inst 1987; 52:5-21]. Mangin's approach is referred to herein as GMM. This approach uses an iteratively re-weighted least-squares fitting in which the weight of each data point is set to a function of the residuals of the previous iteration. The GMM method ensures that potentially artifactual data points having large residuals are given lower weights in the estimation of the tensor parameters. Clearly, this approach is statistically more robust than the standard least squares methods in the presence of outliers. However, by using the residuals as the only determinants of the weights, it discards the information contained in the known distribution of errors related to thermal noise.

The other technique or "robust" estimator for robust diffusion tensor estimation, referred to as RESTORE (for robust estimation of tensors by outlier rejection) uses iteratively re-weighted least-squares regression to identify potential outliers and subsequently exclude them. Results from both simulated and clinical diffusion data sets indicate that the RESTORE method improves tensor estimation compared to the commonly used linear and nonlinear least-squares tensor fitting methods and a recently proposed method based on the Geman-McClure M-estimator. The RESTORE method could potentially remove the need for cardiac gating in DWI acquisitions and should be applicable to other MR imaging techniques that use univariate or multivariate regression to fit MRI data to a model [Lin-Ching Chang, Derek K. Jones, and Carlo Pierpaoli, "RESTORE: Robust Estimation of Tensors by Outlier Rejection", Magn. Reson. Med. 53: 1088-1095 (2005)].

Figure 1B:
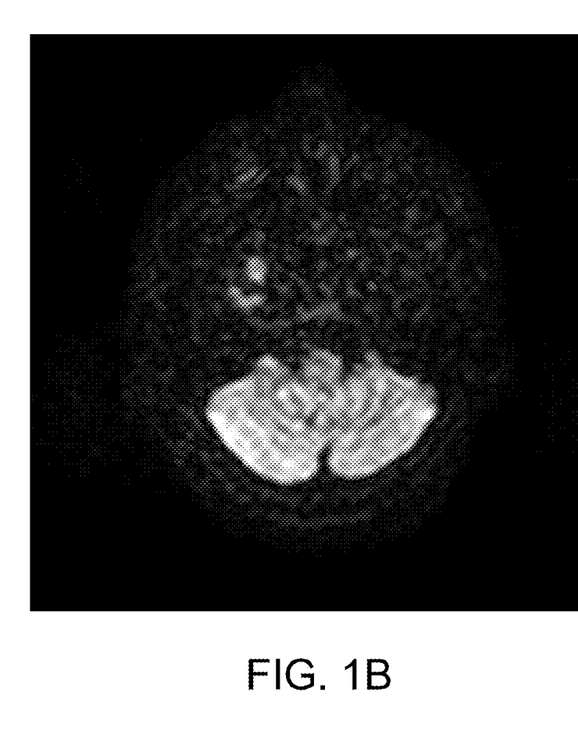

As is known to those skilled in the art, MRI data of a volume is usually acquired by essentially dividing the volume into a plurality of slices and performing 2-D imaging in each slice. When performing DTI-MRI, one would acquire one non-diffusion image and the 6 or more diffusion weighted images for each slice, where one slice of MR images typically consists of 64×64~256×256 pixels. The tensor fitting is performed for every pixel independently and in the RESTORE technique, the handling of outliers, is done for each pixel separately as well. In other words, in RESTORE one estimates the tensor in the presence of data and does not attempt to eliminate corrupted images. As can from a comparison of the corrupted and uncorrupted images of FIGS. 1A and B, when an image is corrupted the corruption for example by tissue motion does not affect the image each pixel independently but rather there are clusters of pixels that that loose or gain abnormal pixel intensity. This is simply because tissue motion happens independent of the pixel size.

There also is a manual technique in which every image that is acquired is visually inspected by a clinician or person knowledgeable in interpreting the particular anatomical images to determine if any of the images display corruption. If corruption of an image is detected, the clinician can exclude the acquired image from being used further in the DTI-MRI process. Needless to say the visual inspection process is time consuming and subject to error given the large number of images that would have to be evaluated when SNR is taken into consideration. For example, if the volume was divided into 50 slices and 60 diffusion weighted images where acquired for each slice, then about 3000 (50×60) images would be acquired and evaluated. There presently is no existing technique by which corrupted images are detected other than by such a manual visual inspection process.

It thus would be desirable to provide methods and MRI systems that automatically evaluate the quality of the acquired raw images and remove corrupted images from the subsequent tensor fitting. It also would be particularly desirable to provide such methods and MRI systems that would allow such an evaluation to be performed post acquisition of image data and/or during the image data acquisition process (i.e., essentially in real time). It also would be particularly desirable to provide such methods and MRI systems that would allow the image acquisition process to acquire additional image data to replace image data that is determined to be corrupted by such an evaluation. It also would be particularly desirable to provide MRI systems that embody computer applications programs or computer implemented methods that embody such methods that automatically evaluate the quality of the acquired raw images and remove corrupted images from the subsequent tensor fitting. It also would be desirable to provide such methods and MRI systems that would not require users having greater skills or abilities than those who routinely perform MRI processed and operate magnetic resonance imaging apparatuses and systems.

SUMMARY OF THE INVENTION

The present invention features a method for automatically evaluating acquired MRI data and determining the quality of the acquired images and for removing the image data for corrupted images from the subsequent tensor fitting based on such evaluating and determining.

In further embodiments, such evaluating includes performing LMSE tensor estimation, DWI fitting, residual error mapping and creation of quality maps.

In further embodiments, such determining includes judging the quality of the image data to determine if the image data satisfies a quality threshold criteria and if determined not to be satisfied, adjudging the image to be corrupted. Such methods also include generating a tensor map if it is adjudged and determined that all of the image data satisfies a quality threshold criteria. In further embodiments, such methods include generating a tensor map from the image data of the images remaining after said determining and adjudging.

Such methods include performing said evaluating, determining and removing in real time and in the case where an image is determined to be corrupted, such methods further includes re-acquiring additional image data corresponding to each of the one or more images removed as being corrupted. In this way, the imaging process can respond to a decision to remove an image as being corrupted and acquire additional image data corresponding to a particular image that was removed as being corrupted. In other words, the medical personnel operating the MRI scanner can appropriately configure the MRI scanner to acquire the image data corresponding to a particular image that was removed as being corrupted (i.e., scanner does not have to be configured to re-acquire all the image data all over).

Also featured are MRI scanning systems or MRI systems that embody such methods as well as featuring applications programs for implementing such methods. Also such applications programs can include instructions and criteria as well as code segments for implementing such methods so that such systems are operated or controlled to acquire image data for images determined to be corrupted and removed for purposes of creating a tensor map.

The above-described methods and systems differ from the prior art in that the evaluation for corrupted images is done on an image-by-image basis, whereas the prior art attempts such an evaluation on a pixel by pixel basis. When an image is corrupted, it does not affect the image of each pixel independently. Instead, there should be a cluster of pixels that loose or gain abnormal pixel intensity, because tissue motion happens independent of the pixel size. In the present invention while tensor fitting is performed on a pixel-by-pixel basis, the evaluation of the corruption of the acquired image data is done on an image-by-image basis. This method to perform the image quality assurance is an entirely new approach from the pixel by pixel approach of the prior art as described herein.

In the above-described methods and systems detection is based on identification of outliers in the tensor fitting. While this approach works for many cases, it is possible that the above-described method may not detect outliers when there are more than a certain number of outliers, which could lead the fitting to start to deviate from the real value. According to another aspect/embodiment, the present invention features another technique that is not based on the fitting results.

In this aspect/embodiment, the technique utilizes the continuity or discontinuity of image intensity. In DTI, each imaging slice is acquired independently and the image corruption occurs independent of adjacent image slices. An erroneous signal intensity in one slice causes through-slice intensity "discontinuity" (hereafter interslice intensity discontinuity). In this technique, this discontinuity is quantified and used as one of the parameters to judge corrupted pixels and images. This approach works in a pixel-by-pixel basis but similar to the above-described methodology, clustering can be performed to remove the corrupted pixels or images.

In the present invention, the quality of the raw images is automatically evaluated and corrupted images are removed (automatically removed) from the subsequent tensor fitting. Currently, this type of image quality assurance is not performed in conventional DTI-MRI techniques. The present invention is expected to dramatically improve the quality assurance of DTI-MRI. This method of the present invention is applied to acquired images to improve the quality of the tensor fitting, but it also is within the scope of the present invention to integrate the methodology of the present invention with an MRI scanner or scanning system to perform real-time image quality assurance.

Other aspects and embodiments of the invention are discussed below.

DEFINITIONS

The instant invention is most clearly understood with reference to the following definitions:

A computer readable medium shall be understood to mean any article of manufacture that contains data that can be read by a computer or a carrier wave signal carrying data that can be read by a computer. Such computer readable media includes but is not limited to magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; paper media, such as punched cards and paper tape; or on carrier wave signal received through a network, wireless network or modem, including radio-frequency signals and infrared signals.

DTI-MRI shall be understood to mean a diffusion-weighted tensor magnetic resonance image technique or a diffusion-weighted tensor imaging magnetic resonance image technique.

DWI shall be understood to mean diffusion weighted image and DWIs shall be understood to mean diffusion weighted images.

Interslice intensity discontinuity shall be understood to be describing the case where an erroneous signal intensity in one slice causes a discontinuity in through-slice intensity.

LMSE shall be understood to mean a least square mean error fitting technique.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 2A:
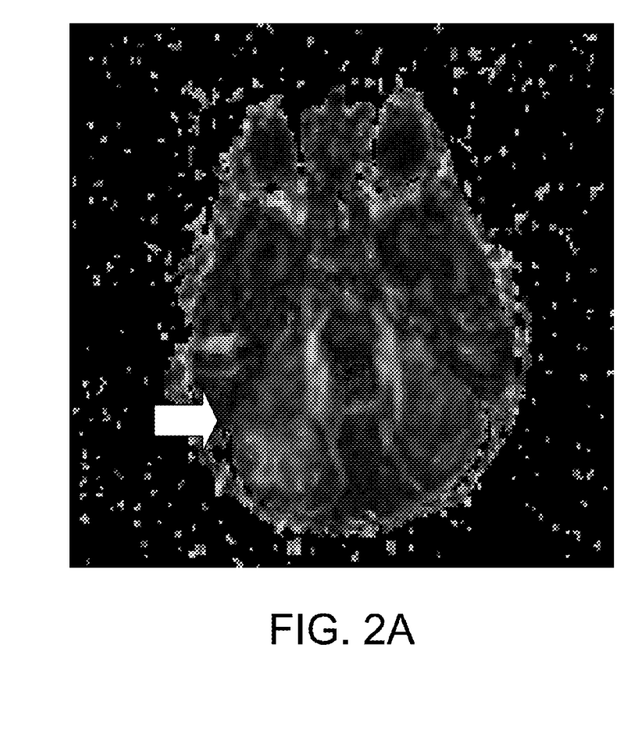
FIG. 2A is an illustration of a DTI image when corrupted images are used for the tensor fitting process.
Figure 2B:
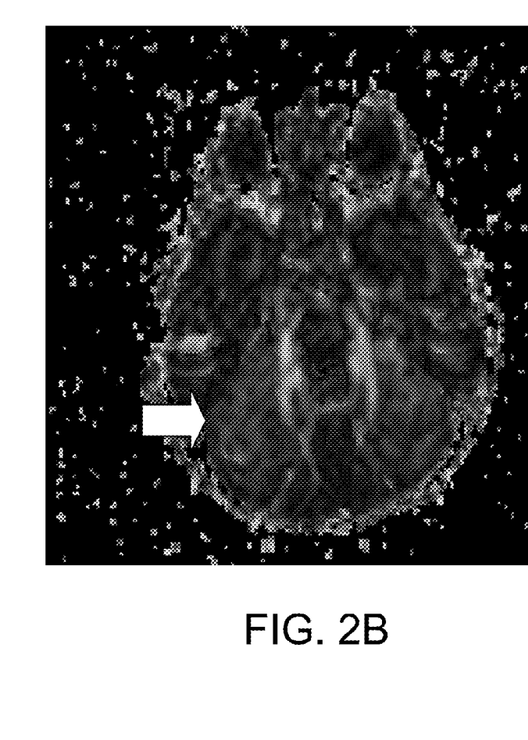
FIG. 2B is an illustration of the DTI image of FIG. 2A, but where corrupted images are removed from use for the tensor fitting process.

The present invention is directed to a method that evaluates the quality of raw images acquired for diffusion tensor imaging (DTI). Because of the high sensitivity of the raw images to subject motion, one or more of the large number of raw images that are typically acquired, are often corrupted. Currently, such corrupted images are used for the subsequent tensor fitting, leading to severe artifacts such as that shown in FIG. 2A. As described herein, there are techniques used that in effect attempt to eliminate the effect of an outliers of the corruption numerically. If corrupted images are removed from the subsequent fitting calculation, however, then the DTI images can be corrected as is shown in FIG. 2B. The present invention also is directed to MRI scanning systems that embody such a methodology, particularly so that such an evaluation can be performed in real time and not be limited to post data acquisition processing.

Such methods and systems are such as to automatically detect corrupted images in raw images (diffusion-weighted images). It also is desirable for the method to yield a report as to the frequency and mode of corrupted images. When a detection of a corrupted image(s) occurs, the method of the present invention also automatically removes the corrupted image(s) from the tensor fitting calculation so as to thereby also correct the resultant corruption-affected DTI images. When the methodology and detection scheme of the present invention is implemented in an MRI scanner, such scanners also can perform real-time monitoring of image quality. This real time monitoring can provide a mechanism during the MRI data acquisition process to identify the need to perform additional scanning so as to in effect reacquire image data corresponding to the removed corrupted image set(s).

Figure 3A:
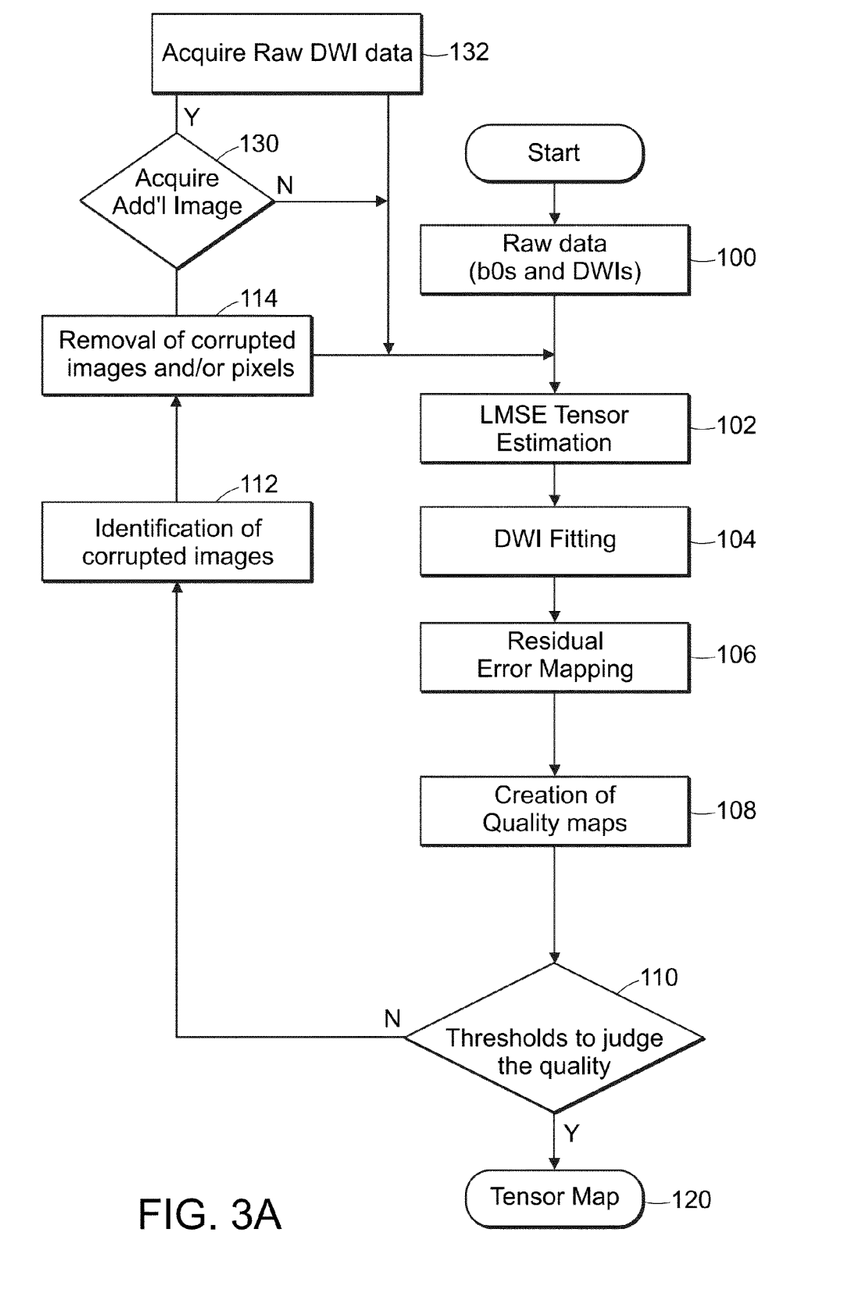
FIG. 3A is an exemplary flow diagram illustrating one process of the present invention.
Figure 3B:
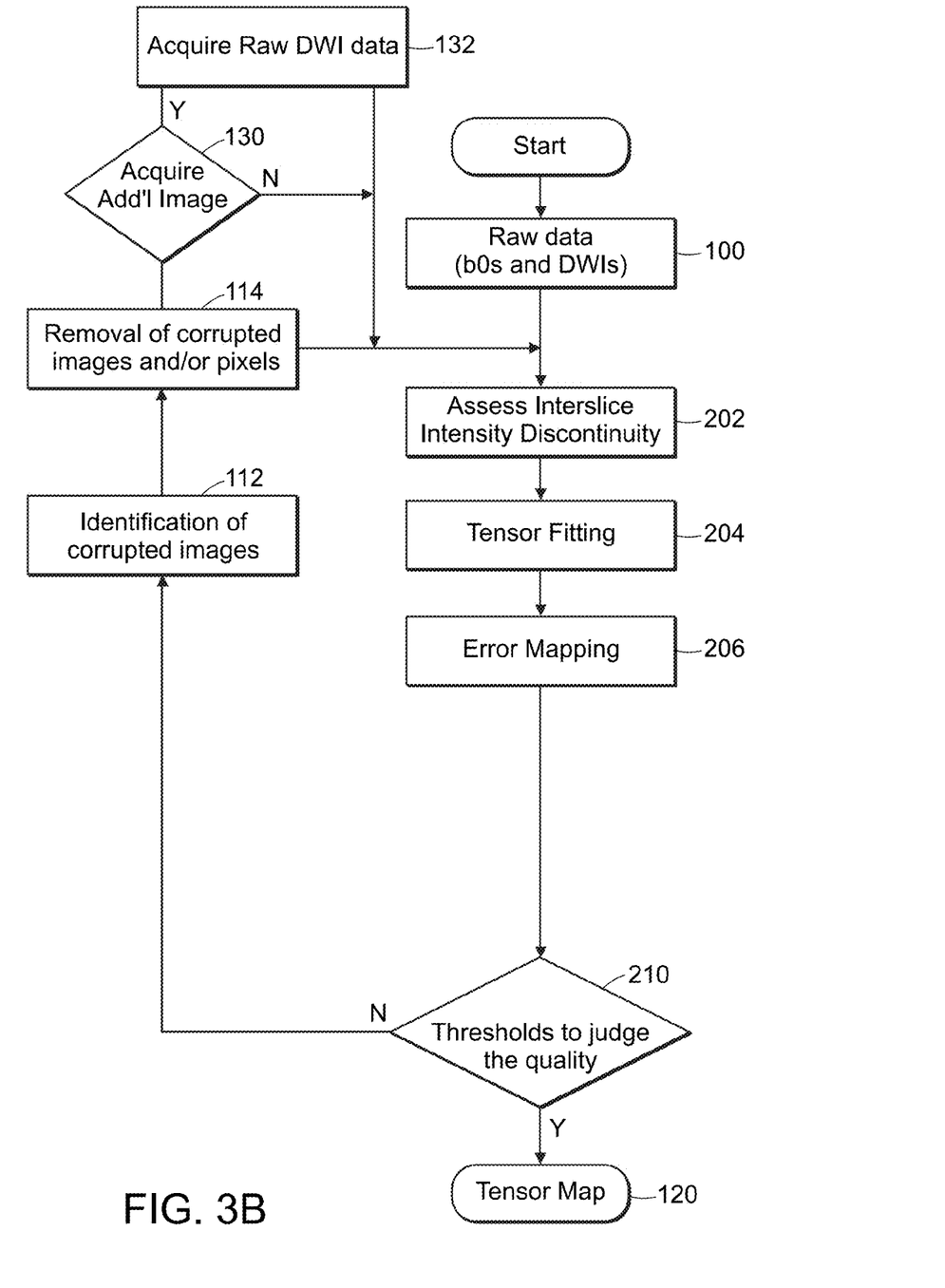
FIG. 3B is an exemplary flow diagram illustrating another process of the present invention.

Referring now to the various figures of the drawing wherein like reference characters refer to like parts, there is shown in FIGS. 3A, B flow charts illustrating methodologies of the present invention. The flow charts herein illustrate the structure of the logic of the present invention as embodied in computer program software for execution on a computer, digital processor or microprocessor. Those skilled in the art will appreciate that the flow charts illustrate the structures of the computer program code elements, including logic circuits on an integrated circuit, that function according to the present invention. As such, the present invention is practiced in its essential embodiment(s) by a machine component that renders the program code elements in a form that instructs a digital processing apparatus (e.g., computer) to perform a sequence of function step(s) corresponding to those shown in the flow diagrams.

Either methodology of the present invention is applied to data for diffusion tensor imaging (DTI), which typically consists of acquiring non-diffusion-weighted images (b0 images) and diffusion-weighted images (DWIs), Step 100. As is known in the art, MRI image data for a volume can be acquired by in effect dividing the volume into two-dimensional slices, acquiring image data for the two dimensional slice and combining the image data of the slices to create the three-dimensional image representative of the volume. As such, there would be non-diffusion-weighted images (b0 images) and diffusion-weighted images (DWIs) for each slice.

As is known to those skilled in the art, at least 6 DWIs are needed to compute a tensor at each pixel. Typically, 12-90 DWIs with various diffusion encoding orientations are acquired for purposes of enhancing signal-to-noise ratio (SNR). As image data acquired may be excluded during such processing as being corrupted, the number of DWIs acquired also might be increased to limit the effect that the elimination of corrupted images would have on SNR.

All the data (b0s and DWIs) are used for pixel-by-pixel tensor calculation, which yields 3×3 diffusion tensor at each pixel. Multi-variate linear least-square fitting is widely used, although non-linear fitting can also be used. For example, diffusion tensor can be calculated using;

$$\ln\left[\frac{S}{S_0}\right] = -\int_0^t \gamma^2 \left[\int_0^{t'} \overline{G(t'')} dt''\right] \cdot \bar{\bar{D}} \cdot \left[\int_0^{t'} \overline{G(t'')} dt''\right] dt'$$

However, the invention is applicable to any form of diffusion-weighted images with or without the above mentioned tensor calculation.

Referring now to FIG. 3A, residual error maps are calculated using for example the following calculations/calculational process (Steps 102-106).

First, the b-matrix was computed from known diffusion orientation vectors $g_k = (g_{kx}, g_{ky}, g_{kz})$ (k=1 ... K, $|g_k|$=1), $$bMatrix = \begin{bmatrix} g_{1x}^2 & g_{1y}^2 & g_{1z}^2 & 2g_{1x}g_{1y} & 2g_{1x}g_{1z} & 2g_{1y}g_{1z} \\ g_{2x}^2 & g_{2y}^2 & g_{2z}^2 & 2g_{2x}g_{2y} & 2g_{2x}g_{2z} & 2g_{2y}g_{2z} \\ \ldots & \ldots & \ldots & \ldots & & \\ g_{Kx}^2 & g_{Ky}^2 & g_{Kz}^2 & 2g_{Kx}g_{Ky} & 2g_{Kx}g_{Kz} & 2g_{Ky}g_{Kz} \end{bmatrix}$$

Second, the LSME method was implemented on the over-determined linear equations for the diffusion tensor estimation by:

$$\begin{bmatrix} D_{xx} \\ D_{yy} \\ D_{zz} \\ D_{xy} \\ D_{xz} \\ D_{yz} \end{bmatrix} = bMatrix^+ \begin{bmatrix} ADC_1 \\ ADC_2 \\ \ldots \\ \ldots \\ ADC_K \end{bmatrix}$$

Where, $D_{xx}$, $D_{yy}$, $D_{zz}$, $D_{xy}$, and $D_{yz}$, are 6 independent components of the tensor matrix, $bMatrix^+$ is the pseudo-inverse of the b-matrix, and $ADC_k$ (k=1 ... K) is the apparent diffusion constant derived from the DWIs.

Before the tensor estimation, if multiple repetition was employed, the standard derivation of multiple-repetition scanning will be calculated for the purpose of image quality judgment later.

Next, the DWI-fitting procedure was performed using the estimated tensor and b-matrix by following equation:

$$\begin{bmatrix} fDWI_1 \\ fDWI_2 \\ \ldots \\ \ldots \\ fDWI_K \end{bmatrix} = bMatrix \begin{bmatrix} D_{xx} \\ D_{yy} \\ D_{zz} \\ D_{xy} \\ D_{xz} \\ D_{yz} \end{bmatrix}$$

Where, fDWI stands for fitted-DWI.

The results of this fitting step were then subtracted against the original DWIs over all pixels of each slice, resulting in so called error maps.

After the error maps are created, there are several ways to create "Quality maps" Step 108, with which image quality can be judged by simple thresholds. This quality map can be a single scalar map or multiple maps with multiple thresholds. For example, the following procedures can be used separately or combined.

Clustering Analysis with Autocorrelation:

Let I(i,j) be the intensity of the error-map at the point (i,j), if the error-map has mean value $\mu$ and standard derivation $\sigma$ then the definition of n-lag auto-correlation is:

$$AutoCorr(n) = \frac{E[(I(i,j) - \mu)(I(i \pm n, j + n) - \mu)]}{\sigma^2}$$

Where, E[X] is the expected value of X.

The outlier is supposed to have higher coefficient values due to the residuals error clustering caused by the corruption. In this way, an image quality criterion is defined according to the statistics of the auto-correlation functions over all error-maps to judge the outliers. For example, let $\mu_{AutoCorr}$ and $\sigma_{AutoCorr}$ be the mean value and standard derivation of Auto-Corr(.) over all error-maps, and Threshold a pre-defined threshold value, If(AutoCorr(n)−$\mu_{AutoCorr}$)>(Threshold*$\sigma_{AutoCorr}$)

Creation of Standard Deviation Maps of the Error Maps:

A standard deviation map can be calculated from the error maps (Stdev(Error map)). For example, if there are 12 DWIs, there will be 12 error maps. If one of the DWIs is corrupted, there should be areas with very high standard deviation. A normalized Stdev(Error map) can be calculated;

Normalized Stdev(Error map)=Stdev(Error map)/Error map

By applying a threshold, for example, 10%, a binary mask of outlier pixels can be generated. This map can be fed into the cluster analysis described above.

Creation of Difference or Standard Deviation Maps of Repeated Measurements

If there are repeated datasets, various quality maps can be generated by using the fact that the repeated measurements should be identical. For example, difference (two repetitions) or standard deviation (more than 3 repetitions) can be generated, in which image corruption can be clearly identified because of its non-reproducible nature.

After the quality maps are generated and thresholds are set, all DWIs are evaluated to adjudge the quality of the images that were acquired, Step 110. The DWIs are evaluated either by absolute criteria (e.g., rejected if there are bad pixels more than thresholds) or by relative criteria (e.g., sort the DWIs and reject the worst one). If as a result of the evaluation it is determined that all of the DWIs are acceptable (Yes, Step 110), the tensor fitting is performed iteratively and a tensor map is generated, Step 120.

If as a result of the evaluation it is determined that one or more of the DWIs or pixels being evaluated are not acceptable and thus, considered to be a corrupted DWI (No, Step 110), then each of the one or more rejected DWI(s) or pixel(s) is identified, Step 112 and the identified DWI(s) or pixel(s) is removed, Step 114. As such removal, the imaged data corresponding to the rejected DWI or pixel can be deleted, or flagged as not to be used, or otherwise prevented from being used in the tensor fitting procedure using any of a number of techniques known to those skilled in the art.

According to further embodiment of the present invention, after removing the corrupted image or DWI (Step 114), a decision is made to determine if more image data or DWI(s) should be acquired to replace each specific DWI(s) that was removed because it had been determined to be corrupted, Step 130. If the decision is to reacquire additional image data for a given removed DWI, then raw data for the specific DWI(s) is acquired, Step 132. In other words, the MRI scanner is configured to establish the same conditions (e.g., same gradient fields) that were present when the image data was acquired for each of the removed DWIs. After acquiring the image data (Step 132), or after deciding that image data is not to be acquired (No, Step 130) or after removing the corrupted image(s) if the process does not include steps 130-132, the process returns to Step 102 and the process continues until a favorable decision is reached in step 110.

Referring now to FIG. 3B, there is shown another methodology of the present invention that is applied to data for diffusion tensor imaging (DTI). Reference should be made to the discussion above for details of the method step(s) that are commonly numbered with FIG. 3A that is/are not otherwise discussed below. As indicated above, such a methodology typically consists of acquiring non-diffusion-weighted images (b0 images) and diffusion-weighted images (DWIs), Step 100. In this methodology the residual error map(s) are calculated using for example the following process of assessing interslice intensity discontinuity (Step 202), tensor fitting (Step 204) and residual error mapping (Step 206) in which interslice intensity discontinuity is incorporated in the tensor fitting. The fitting routine for such tensor fitting can be any of a number of routines known to those skilled in the art or hereinafter developed and include for example a simple tensor fitting routine such as linear fitting as well as robust fitting.

For the judgment of the intensity discontinuity, there are several ways for quantification. For example, simple subtraction between the adjacent slices could detect large discontinuity. Another effective way is to create an average DWI from all DWIs, which serves as a reference image and subtract individual DWIs. These images can be served as the error map in 206. Here we also demonstrate a more sophisticated approach. For each DWI image which includes multislice 2D slices (referred to herein as I1), a nonlinear interpolation of the intensity through the slices is performed to remove sudden intensity changes between slices. The interpolated image is referred to herein I2. The difference of interpolated and original image (referred to herein as I3) is called the intensity discontinuity map of I1. To eliminate the intensity discontinuity caused by real (non-artifact) anatomical changes between slices, the I3 is further abstracted from a reference image (referred to herein as Ir), where Ir is the intensity discontinuity map of non-diffusion-weighted image (referred to herein as b0 image). This intensity discontinuity map of non-diffusion-weighted image is not sensitive to subject motions as much as the DWIs.

The Ir image is generated in the same way as the generation of I3 except the input is b0 not DWI. A corrected intensity discontinuity map (referred to herein as I4) is created using the following relationship I4=|I3−Ir|. The value at each pixel of the corrected intensity discontinuity map is used in the tensor estimation or fitting procedure as a weighting factor. For example, the formula of the fitting $$\rho(\epsilon_i) = \epsilon_i^2/(\epsilon_i^2 + C^2)$$

as provided in Mangin et al. [Mangin J F, Poupon C, Clark C, Le Bihan D, Bloch I. Distortion correction and robust tensor estimation for MR diffusion imaging. Med Image Anal 2002; 6:191-198] is modified to be $$\rho(\epsilon_i) = \epsilon_i^2/((a(I_{4i})^2 + 1)(\epsilon_i^2 = C^2))$$

where a is a preset normalization factor, $I_{4i}$ is the value of the corrected intensity discontinuity map value of the ith diffusion gradient. Thereafter, the estimated DWI is subtracted from the original DWI to generate an error map (Step 206).

A thresholding method is used to detect the points with large error and thus generate a binary mask. The connected components in the mask are evaluated to determine if the area of the connected components is greater than a preset threshold (Step 210). Alternatively, the DWIs are evaluated either by absolute criteria (e.g., rejected if there are bad pixels more than thresholds) or by relative criteria (e.g., sort the DWIs and reject the worst one). If as a result of the evaluation it is determined that all of the DWIs are acceptable (Yes, Step 210), the tensor fitting is performed iteratively and a tensor map is generated, Step 120.

If as a result of the evaluation it is determined that one or more of the DWIs or pixels being evaluated are not acceptable and thus, considered to be a corrupted DWI (No, Step 210), then each of the one or more rejected DWI(s) is identified, Step 112 and the identified DWI(s) or pixel(s) is/are removed, Step 114. As indicated above, the imaged data corresponding to the rejected DWI or pixels can be deleted, or flagged as not to be used, or otherwise prevented from being used in the tensor fitting procedure.

In further embodiments, after removing the corrupted image or DWI (Step 114), a decision is made to determine if more image data or DWI(s) should be acquired to replace each specific DWI(s) that was removed because it had been determined to be corrupted, Step 130. If the decision is to reacquire additional image data for a given removed DWI, then raw data for the specific DWI(s) is acquired, Step 132. After acquiring the image data (Step 132), or after deciding that image data is not to be acquired (No, Step 130) or after removing the corrupted image(s) if the process does not include steps 130-132, the process returns to Step 202 and the process continues until a favorable decision is reached in step 210.

Figure 4:
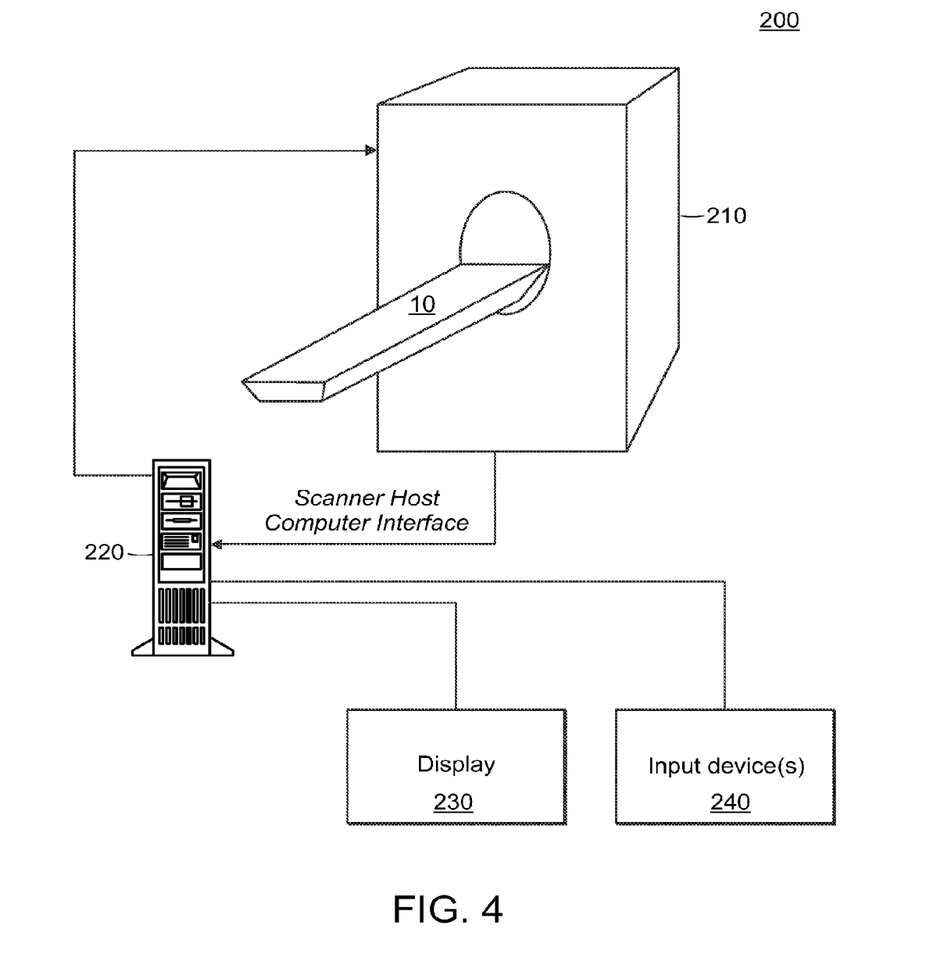
FIG. 4 is a schematic view of an exemplary MRI system.

Referring now to FIG. 4, there is shown a schematic view of an exemplary scanning system 200 including an assembly 210 including among other things the main magnet, gradient coils, detection coil(s) and related receivers, and excitation RF transmitter all of which cooperate to create the conditions necessary for acquiring magnetic resonance signals from the object, patient or person being imaged. Typically, the object, patient or person to be imaged is placed on a table, bed 10 or other structure that is moved into the area of effect of the main and gradient magnets when MRI data is to be acquired and removed therefrom for example upon completion of data acquisition.

The assembly 210 is operably coupled to the host computer 220 on which an applications program(s) is stored or loaded for execution on the host computer 220. The applications program(s) controls operation of the gradient coils, RF transmitter and detection receivers for acquisition of data and controls processing of acquired data, where applicable. Also operably and communicatively coupled to the host computer 220 are a display 230 (e.g., CRT, LCD) and one or more input devices 240 (e.g., keyboard. mouse).

In further embodiments of the present invention, an applications program is provided for execution on the host computer 220 for processing acquired DWI data. Such an applications program includes instructions and criteria as well as code segments for processing the DWI data as described herein to automatically evaluate and assess the acquired DWIs to determine if any of the acquired DWIs are corrupted and to provide an output, for example to the operator of the scanning system 200, identifying the corrupted DWI(s). In addition, the applications program further includes instructions to remove the corrupted DWI(s).

In further embodiments, the applications program includes instructions and criteria for also positing an inquiry to the system operator whether to perform additional scans at the conditions under which image data had been previously acquired for the corrupted DWI(s), in other words whether to acquire image data under these conditions. In response to an affirmative response, the applications program further includes instructions and criteria to cause such additional scans to be performed and to acquire additional image data. In yet further embodiments, the applications program also would again evaluate and assess the additionally acquired DWI(s) to determine if any of the additional acquired DWI(s) was corrupted, essentially repeating the process described above. In alternate embodiments, the applications program further includes instructions and criteria for causing such performing of additional scans, acquiring additional image data and such evaluating and assessing to be performed automatically.

EXAMPLE

Introduction:

Diffusion tensor imaging (DTI) and DTI-based axonal mapping are used increasingly as important tools in clinical research for their ability to study brain white matter anatomy and abnormalities. Diffusion tensor maps are typically calculated by the least square mean error (LSME) fitting of signal intensities from diffusion weighted images as a function of the corresponding b-matrices derived for the diffusion orientation vectors. In practice, diffusion weighted images (DWIs) are usually influenced by both thermal acquisition noise and varying artifacts. The LSME fitting takes into account the thermal noise which is assumed additive and is modeled approximately by a zero-mean Gaussian distribution. However, the signal variability is influenced not only by thermal noise but also by varying artifacts such as temporally and spatially subject motions and cardiac pulsations which do not follow Gaussian distributions. Noisy DWIs can cause the estimated diffusion tensor to be erroneous. In this example, we introduced the feedback theory into tensor fitting procedure and proposed a novel approach to improve the robustness of the tensor estimation by automatic outlier rejection.

Methods:

An algorithm embodying the methodology of the present invention was implemented on a computer and MRI image data including image data obtained using a DTI-MRI technique was processed using such an algorithm and the acquired image data. In particular, the algorithm was implemented on a Windows platform with a user-friendly interface and had been incorporated into our in-house program DTI-Studio. In accordance with the computer implemented algorithm/method the following steps were performed.

First, the b-matrix was computed from known diffusion orientation vectors. Second, the LSME method was implemented on the over-determined linear equations for the diffusion tensor estimation. Next, the DWI-fitting procedure was performed using the estimated tensor and b-matrix. The results of this fitting step were then subtracted against the original DWIs over all pixels of each slice, resulting in so called error-maps.

Afterwards, the goodness-of-fitting was evaluated based on the statistic measurements of the error-maps. Auto-correlation coefficients were used as the measurements for this evaluation. Outliers are supposed to have higher coefficient values due to the residuals error caused by varying artifacts. If the goodness of fitting criterion was not satisfied, the outliers were identified and the iterative tensor estimating process was launched again after the outliers were excluded.

The whole procedure continued iteratively until the goodness criterion was satisfied or reached a pre-defined maximum iteration number.

Figure 5:
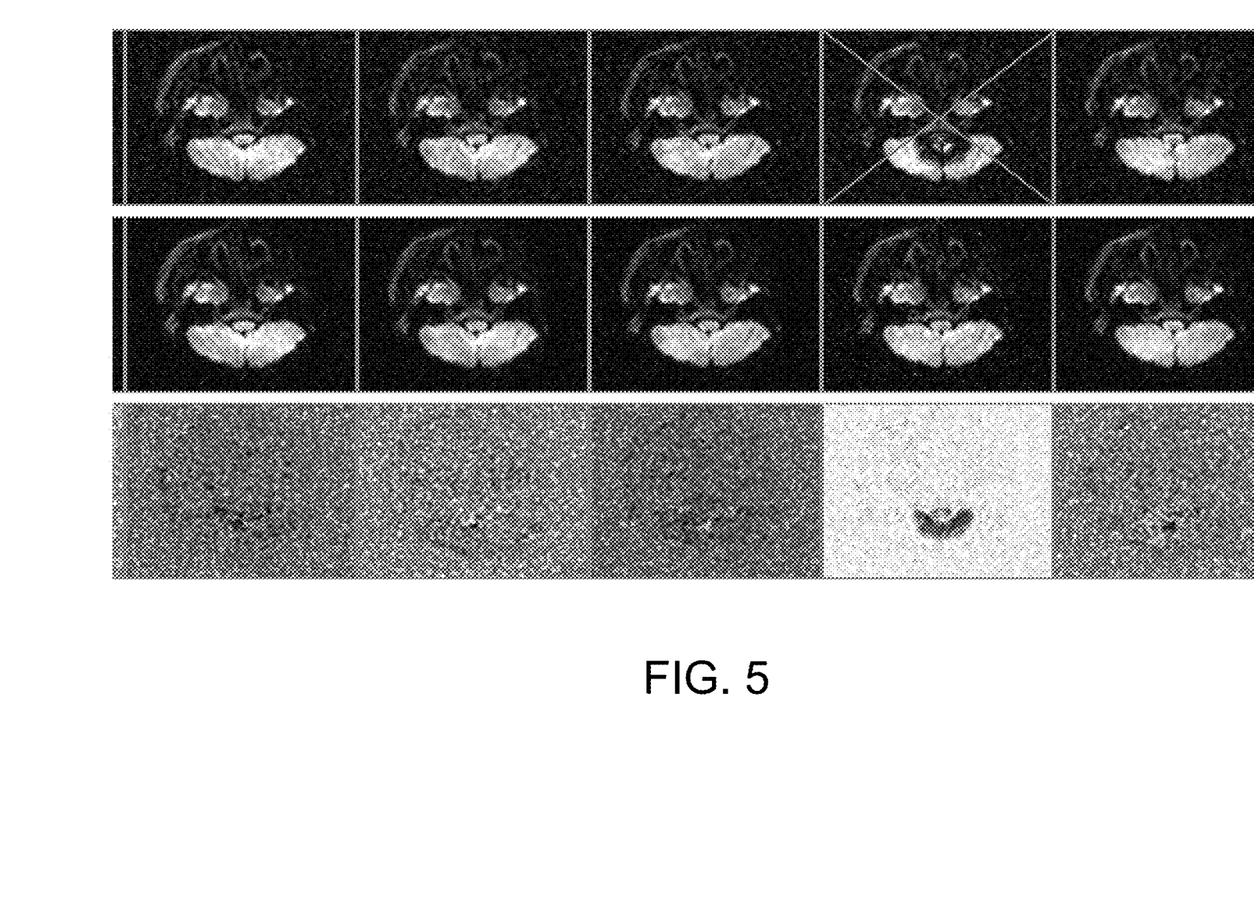
FIG. 5 is an illustrative screen shot of the algorithm of the present invention implemented on a computer. The first row shows the original DWIs in different orientations. The second row shows the re-calculated DWIs after the first iteration of the tensor estimation. The third row shows the error-maps between the original and the "ideal" DWIs. The outlier was identified, marked with a red X, and would be excluded in the second iteration.

Results and Discussion:

There is shown in FIG. 5, a screen shot of the program in action. The outlier being diagnosed in the first iteration is crossed out with an X in this example.

Artifacts are common in clinical DWIs due to the intrinsic low resolution and related imaged distortions of the image acquisition techniques. Of these, the subject motion when scanning uncooperative patients and residual error from cardiac pulsation are the dominant sources of the observed motion-related artifacts. These artifacts do not follow Gaussian distributions. When no corrupted data were included, all fitting methods showed similar results. In the presence of outliers, especially those orienting from non-Gaussian temporally varying artifacts, the computer implemented algorithm/method embodying the methodology of the present invention proved to be a good approach to improve the accuracy of the estimated tensor with respect to the commonly used fitting methods. It also was noted that the computation time was not increased significantly as compared with the linear LS methods that we used before.

Despite the good performance of the algorithm, this approach or method relies on data redundancy. Thus, to avoid problems from arising, the original dataset should have enough orientations or repetitions to correctly identify and exclude the outliers. The number of good data can be also an influence factor on the performance of the algorithm.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for diffusion tensor magnetic resonance imaging (DTI-MRI) comprising the steps of:
   acquiring MRI data for non-diffusion weighted images and MRI data for diffusion weighted images (DWI(s));
   evaluating the acquired data using an algorithm and determining if any of the acquired DWI(s) is corrupted;
   automatically removing the DWI(s) or pixel(s) determined to be corrupted; and
   reacquiring data for the removed DWI(s) or pixel(s) to re-evaluate the data;
   wherein said evaluating, determining, removing, and reacquiring are performed in real time during initial acquisition of the MRI data and prior to complete acquisition of all of the MRI data.

2. The DTI-MRI method of claim 1, further comprising the steps of:
   performing tensor fitting using the MRI data after the removed DWI(s) or pixel(s) are reacquired.

3. The DTI-MRI method of claim 1, wherein said evaluating and determining includes:
   judging the quality of each of the acquired DWI to determine if the DWI being judged satisfies a quality threshold criteria; and
   adjudging the DWI to be corrupted if it is determined that DWI or pixel being judged does not satisfied the criteria.

4. The DTI-MRI method of claim 3, wherein said judging and adjudging is repeated for each acquired DWI and wherein said method further comprises the steps of
   automatically removing the DWI(s) or pixel(s) so adjudged to be corrupted; and
   performing tensor fitting using the MRI data for those DWI(s) or pixel(s) not adjudged as being corrupted.

5. The DTI-MRI method of claim 1, further comprising the steps of:
   acquiring additional MRI data for additionally acquired DWI(s) at the conditions under which MRI data for each of the corrupted DWI(s) was acquired.

6. The DTI-MRI method of claim 5, wherein said evaluating and determining includes evaluating the acquired additional MRI data using an algorithm and determining if any of the additionally acquired DWI(s) is corrupted and wherein said method further comprises the steps of:
   automatically removing the additionally acquired DWI(s) determined to be corrupted; and
   performing tensor fitting using the MRI data for those DWI(s) remaining after said removal.

7. The DTI-MRI method of claim 1, wherein said evaluating includes:
   performing LMSE tensor estimation;
   DWI fitting;
   residual error mapping; and
   creating of quality maps.

8. The DTI-MRI method of claim 1, wherein said evaluating includes:
   evaluating the acquired data using an algorithm utilizing an assessment of through-slice intensity information and determining if any of the acquired DWI(s) or pixel(s) is corrupted.

9. The DTI-MRI method of claim 8, wherein in the algorithm the through-slice intensity information is used for fitting weighting for each data point.

10. The DTI-MRI method of claim 8, wherein an image corresponding to the acquired MRI data for non-diffusion weighted images is used as a reference image in the algorithm for estimating an intensity discontinuity caused by anatomy.

11. The DTI-MRI method of claim 1, wherein said evaluating includes:
    generating an intensity discontinuity map for each acquired DWI;
    generating a corrected intensity discontinuity map using the generating an intensity discontinuity map and the acquired MRI data for a corresponding non-diffusion weighted image;
    using a tensor estimation procedure to generate an estimated DWI, where the value at each pixel of the generated corrected intensity discontinuity map is used as weighting factor in the tensor estimation procedure; and
    generating an error map by subtracting the estimated DWI from the acquired DWI.

12. A MRI scanning system configured so as to perform diffusion tensor magnetic resonance imaging (DTI-MRI), said MRI scanning system comprising:
    a MRI data acquiring apparatus to generate the magnetic and RF fields to cause magnetic resonance (MR) signals to be generated by an object being observed;
    a MR signal detection apparatus that detects the generated MR signals and outputs signals representative of image data corresponding to the received MR signals;
    a computer operably coupled to the MR signal detection apparatus that receives and processes the image data; and
    an applications program for execution on the computer, the applications program including code segments, instructions and criteria for:
      evaluating the acquired image data for acquired DWI(s) data using an algorithm and determining if any of the acquired DWI(s) is corrupted;
      automatically removing the DWI(s) or pixel(s) determined to be corrupted;
      automatically removing the DWI(s) or pixel(s) determined to be corrupted; and
      reacquiring data for the removed DWI(s) or pixel(s) to re-evaluate the data;
      wherein said evaluating, determining, removing, and reacquiring are performed in real time during initial acquisition of the MRI data and prior to complete acquisition of all of the MRI data.

13. The MRI scanning system of claim 12, wherein the applications program further includes code segments, instructions and criteria for:
    acquiring additional image data for additionally acquired DWI(s) at the conditions under which image data for each of the corrupted DWI(s) was acquired.

14. The MRI scanning system of claim 13, wherein:
    said evaluating and determining includes evaluating the acquired additional MRI data using an algorithm and determining if any of the additionally acquired DWI(s) is corrupted;
    automatically removing the additionally acquired DWI(s) determined to be corrupted.

15. The MRI scanning system of claim 12, wherein said evaluating, determining further includes code segments, instructions and criteria for:
    judging the quality of each of the acquired DWI to determine if the DWI being judged satisfies a quality threshold criteria; and
    adjudging the DWI to be corrupted if it is determined that DWI being judged does not satisfied the criteria.

16. The MRI scanning system of claim 15, wherein:
    said judging and adjudging is repeated for each acquired DWI; and said automatically removing removes each corrupted DWI(s) so adjudged.

17. The MRI scanning system of claim 12, wherein the applications program further includes code segments, instructions and criteria for:
performing tensor fitting using the data for those DWI(s) or pixel(s) after the removed DWI(s) or pixel(s) are reacquired.

18. A non-transitory storage medium on which is stored an applications program that is executable on a computer, said applications program including code segments, instructions and criteria for:
evaluating the acquired image data for acquired DWI(s) data using an algorithm and determining if any of the acquired DWI(s) or pixel(s) is corrupted;
automatically removing the DWI(s) determined to be corrupted;
reacquiring data for the removed DWI(s) or pixel(s); and
performing tensor fitting using the data for those DWI(s) pixel(s) after the removed DWI(s) or pixel(s) are reacquired to re-evaluate the data,
wherein said evaluating, determining, removing, and reacquiring are performed in real time during initial acquisition of the MRI data and prior to complete acquisition of all of the MRI data.

* * * * *